US00PP18647P2

(12) United States Plant Patent
Oudshoorn

(10) Patent No.: US PP18,647 P2
(45) Date of Patent: Mar. 25, 2008

(54) *PAPAVER* PLANT NAMED 'RUFFLED PRINCESS OF ORANGE'

(50) Latin Name: *Papaver orientale*
Varietal Denomination: Ruffled Princess of Orange

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/520,894

(22) Filed: Sep. 14, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Papaver* plant named 'Ruffled Princess of Orange', characterized by its upright plant habit; moderately vigorous growth habit; and large flowers with ruffled dark orange-colored petals.

2 Drawing Sheets

Botanical designation: *Papaver orientale.*
Cultivar denomination: 'Ruffled princess of orange'.

BACKGROUND OF THE INVENTION

The present invention relates to a new and distinct cultivar of *Papaver,* botanically known as *Papaver orientale* and hereinafter referred to by the name 'Ruffled Princess of Orange'.

The new *Papaver* originated from an open-pollination in 2001 of an unnamed selection of *Papaver orientale,* not patented, as the female, or seed, parent with an unknown selection of *Papaver orientale,* as the male, or pollen, parent. The new *Papaver* was discovered and selected by the Inventor as a single flowering plant from within the progeny of the stated open-pollination grown in a controlled environment in Rijpwetering Wetering, The Netherlands in 2005.

Asexual reproduction of the new cultivar by divisions in Rijpwetering, The Netherlands has shown that the unique features of this new *Papaver* are stable and reproduced true to type in successive generations.

SUMMARY OF THE INVENTION

Plants of the cultivar Ruffled Princess of Orange have not been observed under all possible environmental conditions. The phenotype may vary somewhat with variations in environment such as temperature and light intensity without, however, any variance in genotype.

The following traits have been repeatedly observed and are determined to be the unique characteristics of 'Ruffled Princess of Orange'. These characteristics in combination distinguish 'Ruffled Princess of Orange' as a new and distinct cultivar of *Papaver:*

1. Upright plant habit.
2. Moderately vigorous growth habit.
3. Large flowers with ruffled dark orange-colored petals.

Plants of the cultivar Ruffled Princess of Orange differ from plants of the parent selections and other Papaver cultivars known to the Inventor in plant height as plants of the new Papaver are more compact than plants of the parent selections and other cultivars known to the Inventor.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Papaver.*

The photograph on the first sheet is a side perspective view of a typical of 'Ruffled Princess of Orange' grown in an outdoor nursery.

The photograph at the top of the second sheet is a close-up view of a typical flower of 'Ruffled Princess of Orange'.

The photograph at the bottom of the second sheet is a close-up view of a typical leaf of 'Ruffled Princess of Orange'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the late spring/early summer in an outdoor nursery in Rijpwetering, The Netherlands for about one year. During the production of the plants, day temperatures ranged from 14° C. to 27° C. and night temperatures ranged from 5° C. to 14° C.

Botanical classification: *Papaver orientale* cultivar Ruffled Princess of Orange.

Parentage:

*Female parent.*—Unnamed selection of *Papaver orientale,* not patented.

*Male parent.*—Unknown selection of *Papaver orientale,* not patented.

Propagation:

*Type.*—By divisions.

*Root description.*—Thick, fleshy; light brown in color.

Plant description:

*Form.*—Herbaceous perennial flowering plant, mostly upright; columnar. Basally branching, rosette; flowering stems arise from the base. Moderately vigorous growth habit.

1. *Plant height.*—About 82 cm.

*Plant width.*—About 80 cm.

*Branch description.*—Arrangement: Basal branching; about six basal branches develop per plant. Length: About 71.9 cm. Diameter: About 9 mm. Internode length: About 15.9 cm. Strength: Strong. Aspect: Upright. Texture: Pubescent; rough. Color: 144A.

Foliage description:

*Arrangement.*—Alternate, simple.

*Length.*—About 31.5 cm.

*Width.*—About 15.8 cm.

*Shape.*—Pinnatifid to pinnatisect.

*Apex.*—Acute.

*Base.*—Cuneate.

*Margin.*—Serrate or doubly serrate.

*Texture, upper and lower surfaces.*—Pubescent; rough.

*Venation pattern.*—Pinnate.

*Color.*—Developing foliage, upper surface: 146A. Developing foliage, lower surface: 138A. Fully expanded foliage, upper surface: 143A; venation, 145D. Fully expanded foliage, lower surface: 138B; venation, 138D.

*Petiole length.*—About 18 cm.

*Petiole diameter.*—About 9 mm.

*Petiole color, upper and lower surfaces.*—144A to 144B.

Flower description:

*Flower arrangement and appearance.*—Large semi-double rotate flowers; flowers terminal and face mostly upright; about six flowers per plant at one time.

*Natural flowering season.*—Continuous flowering from late May to late June in The Netherlands.

*Flower longevity on the plant.*—About three days; flowers not persistent.

*Fragrance.*—None detected.

*Flower buds.*—Length: About 4.2 cm. Diameter: About 4 cm. Shape: Broadly ovate. Texture: Densely pubescent. Color: 143A.

*Flower diameter.*—About 16.9 cm.

*Flower depth* (*height*).—About 10.1 cm.

*Petals.*—Arrangement: About six in two whorls. Length: About 9.7 cm. Width: about 13.8 cm. Shape: Roughly reniform. Apex: Irregular, deeply incised; ruffled in appearance. Margin: Irregular, deeply incised; undulate; ruffled in appearance. Texture, upper and lower surfaces: Smooth, glabrous. Color: When opening and fully opened, upper surface: N30A; towards the base, N34A; irregular central black spot, 202A. When opening and fully opened, lower surface: N30A to N30B; towards the base, 31A; at base, N34A.

*Sepals.*—Arrangement: About three in a single whorl. Length: About 1.3 cm. Width: About 1.4 cm. Shape: Pinnatisect. Apex: Acute. Margin: Serrate. Texture, upper and lower surfaces: Densely pubescent. Color, upper and lower surfaces: 145B to 145C; towards the apex, 143A to 143B.

*Peduncles.*—Length: About 71.9 cm. Diameter: About 9 mm. Strength: Strong. Texture: Pubescent; rough. Color: 144A.

*Reproductive organs.*—Stamens: Quantity per flower: About 250. Filament length: About 2 cm. Filament color: 202A; towards the base, 186A. Anther shape: Narrowly oblong. Anther length: About 4 mm. Anther color: 202A. Pollen amount: Scarce. Pollen color: N186A to 202A. Pistils: Quantity per flower: About 14. Pistil length: About 1.6 cm. Stigma shape: Narrowly oblong. Stigma color: N186B. Ovary color: 145A.

*Fruits.*—Type: Capsule. Quantity per flower: One. Length: About 2.4 cm. Diameter: About 3.5 cm. Color: 137A.

*Seeds.*—Quantity per fruit: About 750. Length: About 1 mm. Diameter: About 1 mm. Color: 202A to 202B.

Disease/pest resistance: Plants of the new *Papaver* have not been noted to be resistant to pathogens and pests common to *Papaver.*

Garden performance: Plants of the new *Papaver* have exhibited good tolerance to rain, wind, high temperatures of 30° C. and are hardy to USDA Zone 4.

What is claimed:

1. A new and distinct *Papaver* plant named 'Ruffled Princess of Orange' as illustrated and described.

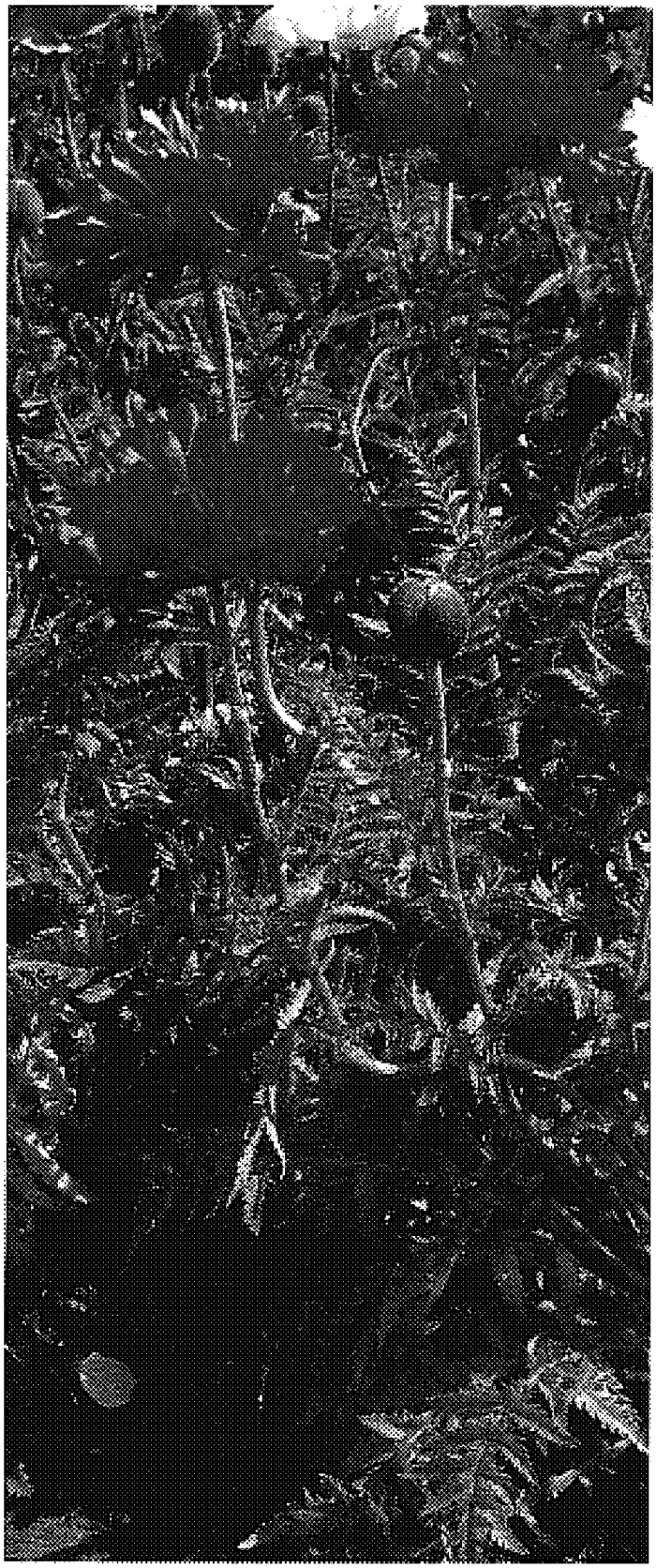

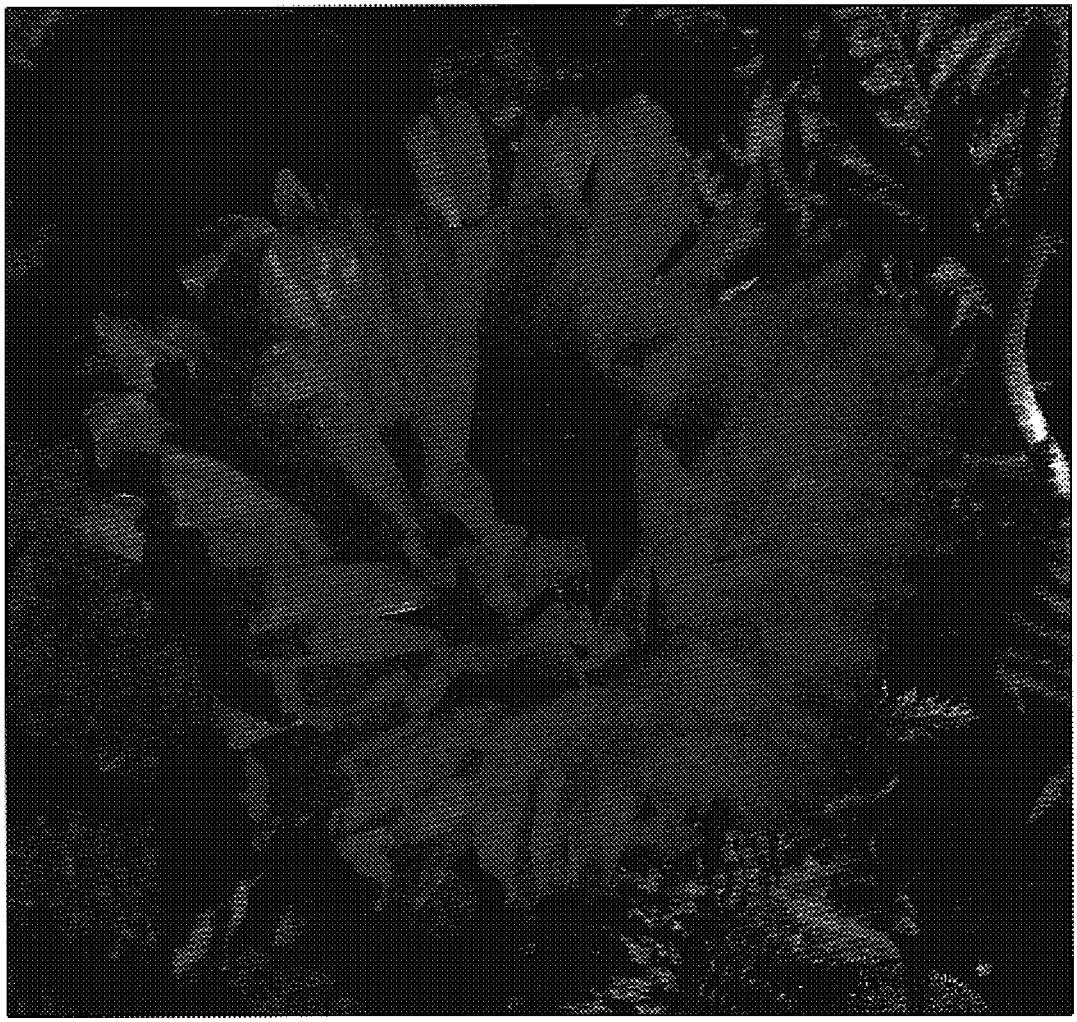
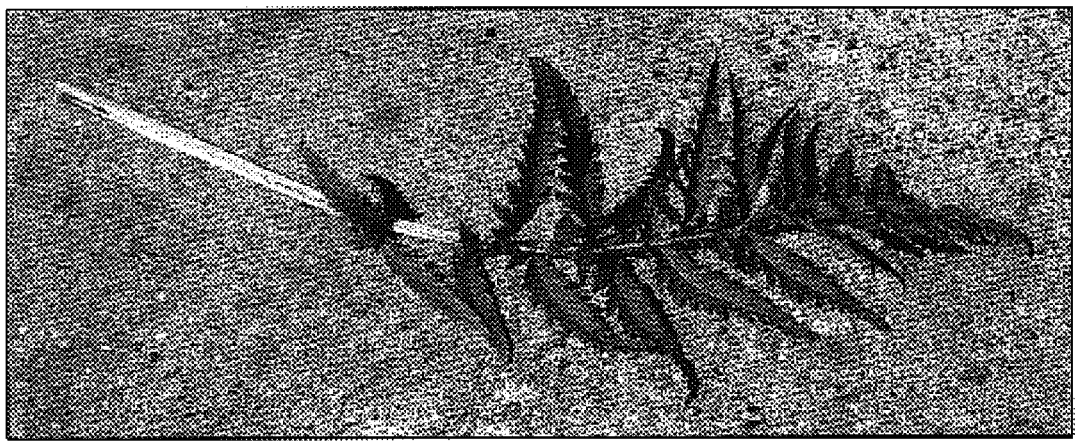

* * * * *